United States Patent [19]
di Palma

[11] Patent Number: 5,022,422
[45] Date of Patent: Jun. 11, 1991

[54] BALL VALVE
[75] Inventor: Giorgio di Palma, Ramona, Calif.
[73] Assignee: IMED Corporation, San Diego, Calif.
[21] Appl. No.: 559,641
[22] Filed: Jul. 30, 1990
[51] Int. Cl.⁵ ............................................. F16K 31/00
[52] U.S. Cl. .................................... 137/15; 251/342; 251/349; 604/246
[58] Field of Search ................ 251/342, 349; 604/246, 604/247; 137/315, 15

[56] References Cited
U.S. PATENT DOCUMENTS

| | | | |
|---|---|---|---|
| 2,831,326 | 4/1958 | Richards et al. | 251/342 |
| 3,006,342 | 10/1961 | Reimann et al. | 251/342 |
| 3,626,959 | 12/1971 | Santomieri | 251/342 |
| 3,819,151 | 6/1974 | Kish | 251/342 |
| 3,851,668 | 12/1974 | Benjamin | 251/342 |
| 4,106,675 | 8/1978 | Taylor | 251/342 |
| 4,142,648 | 3/1979 | Walton | 251/342 |
| 4,730,635 | 3/1988 | Linden | 251/342 |

Primary Examiner—A. Michael Chambers
Attorney, Agent, or Firm—Nydegger & Associates

[57] ABSTRACT

A ball valve device for controlling fluid flow has a stainless steel ball positioned in the lumen of an I.V. tube. The outer diameter of the ball is equal to the inner diameter of the I.V. tube, so that the outer surface of the ball establishes a fluid seal with the inner surface of the tube. A latex sheath surrounds the tube in the proximity of the ball to provide resilience and memory for the tube. Inserts are positioned in the lumen both upstream and downstream from the ball to hold the ball in position under the sheath. Each insert is formed with a lumen for fluid flow, and has a tapered surface adjacent to the ball, which prevents the ball from forming a seal with the insert.

5 Claims, 1 Drawing Sheet

BALL VALVE

FIELD OF THE INVENTION

The present invention pertains to fluid flow control devices. More particularly, the present invention relates to fluid flow control valves which are self-contained within the lumen of the fluid line. Specifically, the present invention pertains to ball valves. The present invention is particularly, but not exclusively, useful for controlling fluid flow in intravenous infusion systems.

BACKGROUND OF THE INVENTION

At the present time, there exist numerous types of valves for occluding or redirecting fluid flow in catheters and intravenous (I.V.) tubes which are commonly used in hospitals and other medical facilities. Because catheters and I.V. tubes necessarily create openings to the internal organs of the body, it is of the utmost importance to maintain a closed, sterile system while these instruments are in place. To this end, valves for occluding fluid flow in I.V. lines are sometimes incorporated within the lumen of the tube to maintain the integrity of the fluid system and prevent airborne contaminants from entering the body. One type of valve well known in the art obstructs fluid flow using a ball in the lumen of the fluid line which snugly fits against the inner walls of the tube. Under normal conditions, such a valve is closed because the tight seal between the ball and the tube completely occludes fluid flow. To open the valve, the tube can be pinched or otherwise deformed to allow flow around the ball, without compromising the sealed interior of the system. Once the pinching pressure is withdrawn, the tube automatically reforms around the ball, to again impede flow. These so-called "ball valves" are generally practical for such intermittent use as collecting small samples of urine from catheters. For a more continuous usage, such as when patients are infused intravenously, it is necessary to maintain a valve in its open, or "free flow", position for extended periods of time. Ball valves generally cannot be kept open for extended periods of time, however, because the plastic tube surrounding the ball tends to permanently deform. Once the tube loses its original shape, a permanent "free flow" condition exists since the ball valve cannot properly reseat to close the fluid line. Ball valves are, however, easy to use and relatively easy to manufacture. Thus, they are desirable for use where possible. For example, a simple ball valve in an I.V. line would permit periodic changes of fluid source, for a patient requiring a continuous flow of medication, without having to change the entire I.V. line each time the solution bag is replaced.

The present invention recognizes the need for an I.V. tube ball valve which can open for extended periods of time, yet maintain its ability to properly reseal. Therefore, the present invention provides a ball valve assembly which can be pinched or otherwise positioned in a free flow condition for extended periods of time without permanently deforming the original shape of the tube. Further, the present invention provides an I.V. tube valve which can be used manually or in conjunction with a pump for extended use. Additionally, the present invention provides a ball valve assembly which is easy to use, relatively inexpensive to manufacture and comparatively cost-effective.

SUMMARY OF THE INVENTION

A preferred embodiment of the I.V. line ball valve assembly in accordance with the present invention includes a stainless steel ball which is positioned in the lumen of the I.V. tube. A latex sheath surrounds the I.V. tube in the vicinity of the ball and is bonded to the tube to provide additional resilience for the tube. The ball is held in position within the lumen of the tube underneath the sheath by an upstream insert and a downstream insert. Preferably, the diameter of the ball is equal to or slightly greater than the inside diameter of the I.V. tube in order to establish an interference fit between the ball and the tubing wall. This "fit" creates a fluid-tight seal in the I.V. line. The upstream and downstream inserts are placed adjacent to the ball to prevent the ball from linear movement in the I.V. line. Each insert is formed with a fluid passageway that permits fluid communication through the tube, and each insert has a tapered surface adjacent to the ball which prevents the ball from occluding the passageway.

As contemplated by the present invention, the ball valve forms a fluid tight seal when the tube is not deformed. The I.V. tube, however, can be deformed in the vicinity of the ball to allow free flow of fluid past the ball. Once the distorting pressure is released, the resilient latex sheath will reform itself along with the I.V. tube to its original shape, reforming a tight seal around the outer surface of the ball.

The novel features of this invention, as well as the invention itself, both as to its structure and its operation, will be best understood from the accompanying drawings, taken in conjunction with the accompanying description, in which similar reference characters refer to similar parts, and in which

DESCRIPTION OF THE PREFERRED EMBODIMENT

Figure 1:
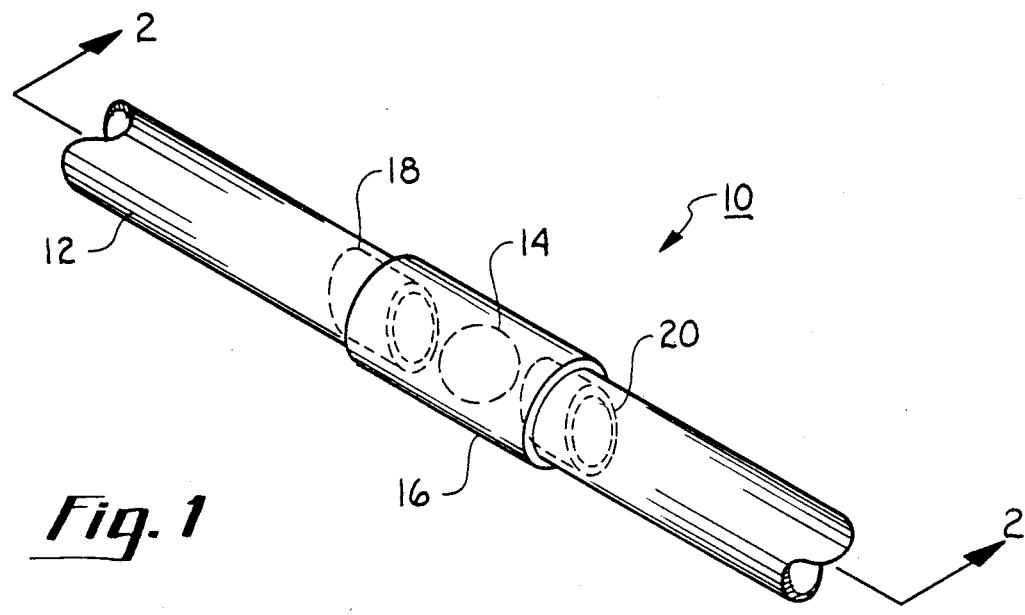
FIG. 1 is a perspective view of the ball valve assembly.

FIG. 1 shows a perspective view of the ball valve assembly, which is generally designated 10. The assembly 10 comprises a section of I.V. tube 12, a stainless steel ball 14 (shown in FIG. 2 and evidenced by the deformation of tube 12 in FIG. 1), a sheath 16 and the inserts 18 and 20 which are shown in phantom in FIG. 1. The I.V. tube section 12 and inserts 18 and 20 are flexible and are made of an appropriate material such as polyvinylchloride (PVC). Sheath 16 is comparatively more rigid than I.V. tube 12 and is made of a resilient material such as latex or silicon.

Figure 2:
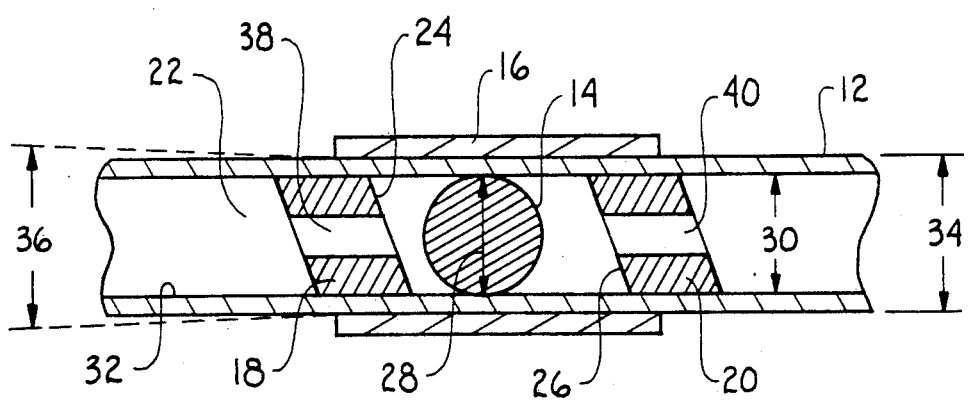
FIG. 2 is a cross-sectional view of the ball valve assembly as seen along the line 2—2 in FIG. 1.

As shown in FIG. 2, stainless steel ball 14 is positioned in the lumen 22 of I.V. tube section 12, with inserts 18 and 20 placed upstream and downstream from ball 14. As shown in FIG. 2, the inserts 18, 20 are respectively formed with fluid passageways 38, 40 which allow fluid flowing through lumen 22 of section 12 to also flow through the inserts 18, 20. Further, insert surfaces 24 and 26 of inserts 18 and 20, respectively, are tapered to prevent the inserts 18, 20 from making a seal between steel ball 14 and the passageways 38, 40 of inserts 18, 20. Consequently, even though steel ball 14 may make contact with inserts 18, 20, the tapered surfaces 24, 26 distance ball 14 from the passageways 38, 40 to leave an opening for fluid flow around steel ball 14 and through the inserts 18, 20.

For the embodiment shown in FIGS. 1 and 2, diameter 28 of steel ball 14 is equal to or slightly greater than inside diameter 30 of tube section 12. As will be appreciated by the skilled artisan, this dimensional relationship establishes a fluid seal between the inside surface 32 of tube section 12 and steel ball 14 when the tube section 12 is not deformed. Similarly, but for a different purpose, the outside diameter 34 of tube section 12 is equal to or greater than inside diameter 36 of sheath 16. As intended for the present invention, a tight fit, or integral connection, between tube section 12 and sheath 16 functions to help prevent tube section 12 from permanently deforming after it has been pinched or otherwise distorted for an extended period of time. Preferably, sheath 16 is bonded to tube section 12 by any means well known in the art such as by solvent bonding. Accordingly, when sheath 16 reforms to its original cylindrical shape, sheath 16 forces tube section 12 to reform as well. Thus, sheath 16 gives a memory quality to tube section 12 comparable with that of the sheath itself.

In its operation, ball valve assembly 10 is operated by mechanically pinching or deforming sheath 16 at the vicinity of steel ball 14. This pinching action disrupts the seal between steel ball 14 and inside surface 26 of tube section 12 and allows fluid to freely flow across ball valve assembly 10. To stop the flow of fluid through valve assembly 10, tube section 12 and sheath 16 are released from the deforming pressure. This release allows sheath 16 to reform itself and consequently cause I.V. tube section 12 to also reform to its original shape. As tube section 12 reforms to its original shape, the fluid seal between the tube's interior surface and the steel ball 14 is reestablished. To prevent steel ball 14 from traveling in the lumen of tube section 12, inserts 18 and 20 are positioned on either side of ball 14 in lumen 22 of tube section 12. Although steel ball 14 may abut against insert surfaces 24 or 26, these surfaces are tapered to prevent a seal from developing between steel ball 14 and either surface.

While the particular ball valve, as herein shown and disclosed in detail, is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. A method for externally controlling fluid flow through a deformable tube which comprises the steps of:
   (a) positioning a ball within the lumen of said tube;
   (b) bonding a resilient sheath to said tube in the vicinity of said ball;
   (c) positioning a first hollow insert and a second hollow insert in the lumen of said tube respectively upstream and downstream of said ball to respectively limit upstream and downstream movement of said ball; and
   (d) mechanically deforming said sheath to allow selective fluid flow past said ball.

2. A ball valve assembly which comprises:
   a deformable tube section having a lumen, said tub section being normally in an undeformed configuration;
   a ball positioned in the lumen of said tube section to establish a fluid seal between said ball and said tube section in its undeformed configuration, said tube section being deformable to allow fluid flow through said tube section around said ball;
   a first hollow insert positioned within said lumen upstream of said ball for limiting upstream movement of said ball in said lumen;
   a second hollow insert positioned within said lumen downstream of said ball for limiting downstream movement of said ball in said lumen; and
   a resilient sheath bonded around said tube section for urging said tube section into its undeformed configuration.

3. A ball valve assembly as recited in claim 1 wherein said first and second inserts are each formed with a passageway to permit fluid flow through said inserts.

4. A ball valve assembly as recited in claim 1 wherein said first and second inserts are each formed with a tapered surface adjacent to said ball.

5. A ball valve assembly as recited in claim 1 wherein said ball is stainless steel and has a diameter equal to or greater than the inside diameter of said tube.

* * * * *